United States Patent [19]

Lang

[11] Patent Number: 4,546,316
[45] Date of Patent: Oct. 8, 1985

[54] MAGNETIC TESTING DEVICE FOR SUPPORTED OBJECTS

[75] Inventor: John G. Lang, Scarborough, Canada
[73] Assignee: Rotesco Limited, Scarborough, Canada
[21] Appl. No.: 394,761
[22] Filed: Jul. 2, 1982
[51] Int. Cl.[4] .................... G01N 27/83; G01R 33/02
[52] U.S. Cl. .................................... 324/262; 324/240
[58] Field of Search ............... 324/217, 218, 228, 235, 324/237–243, 127, 262

[56] References Cited

U.S. PATENT DOCUMENTS

| 4,096,437 | 6/1978 | Kitzinger et al. | 324/235 X |
| 4,388,593 | 6/1983 | Mittleman | 324/262 |
| 4,495,465 | 1/1985 | Tomaiuolo et al. | 324/239 X |

FOREIGN PATENT DOCUMENTS

| 2081907 | 2/1982 | United Kingdom | 324/326 |
| 652479 | 3/1979 | U.S.S.R. | 324/217 |

Primary Examiner—Gerard R. Strecker
Assistant Examiner—Warren S. Edmonds

[57] ABSTRACT

The present invention relates to a testing device for magnetically testing while uninterruptedly moving along an elongated magnetically permeable object having intermittent supports to one side thereof. The device which is arranged to close around the test the object from all sides other than at the supports and to open at and clear past the supports while continuing to move, comprises first and second housing sections hingedly connected to one another with the first housing section being adapted to maintain the device in a testing position relative to the object and the second housing section being moveable relative to the first housing section for opening and closing the device around the object. An actuator is provided for effecting such opening and closing with a control for operation of the actuator without manual assistance at the device.

11 Claims, 9 Drawing Figures

MAGNETIC TESTING DEVICE FOR SUPPORTED OBJECTS

FIELD OF THE INVENTION

The present invention relates to a device for testing for weaknesses in elongated magnetically permeable bodies having intermittent supports to one side thereof and has particular application in the testing of wire ropes used in aerial tram systems.

BACKGROUND OF THE INVENTION

There are many systems which make use of elongated metallic guides for guiding the movement of a body along the guide. The guide itself is supported at spaced intervals which present problems for testing for weaknesses in the guide.

One example of the type of arrangement described above is the standard aerial tram system in which a cable car is supported by rides along a wire rope located above the cable car. This wire rope is supported along its length by spaced apart towers with long stretches of rope between the towers. It is imperative that these long stretches of rope be tested for weaknesses which could affect safety of the system.

There are presently available a number of different types of wire rope testing devices, one of which is a DC wire rope tester which is a device that is arranged to induce a magnetic field in the section of rope located within the device and to test for flux leakages radially of the main magnetic field. These flux leakages are indicative of weaknesses such as fraying or corrosion of the wire rope.

According to standard construction, conventional DC wire rope testers comprise two substantially identical housing sections having strong permanent magnets in each of the housing sections and a search coil located within the tester. In order to use the tester for purposes of checking the strength of the steel wire rope in a cable car system the tester is secured behind one of the cable cars which rides along the steel wire rope pulling the tester with it. The tester itself is wrapped completely around the rope behind the cable car.

This prior art arrangement in extremely awkward to work with due to the presence of the support towers acting as a block to the travel of the tester when it is closed around the rope. Therefore, it is necessary for an individual in the cable car to stop the car in advance of the tower and to climb out onto the cable for opening the tester to allow it to clear past the tower and to then reclose the tester after it has passed by the tower. A manual opening and closing of the tester while the operator is standing out on the cable is time consuming and can be extremly dangerous even under the best of conditions and in curcumstances where the cable is at an awkward angle or where there is inclement weather the difficulties of opening and closing the tester are further increased. Added to this are the difficulties presented by the weight of the housing section that must be opened and closed and the magnetic attraction which has to be overcome to open the tester due to the provision of strong permanent magnets in each of the housing sections.

In an attempt to overcome this problem of clearing the tester past the towers arrangements have been used which comprise only the upper housing section of the tester with the lower housing section being completely removed from the tester. The problem with this particular arrangement is that it does not completely surround the rope and therefore does not provide thorough testing results. For example, the sensors in the upper housing sections may not detect breakages or discontinuities along the lower untested half of the rope.

There are setups other than the cable car system described above which also incorporate elongated magnetically permable guides which have to be tested for strength. These setups again present problems at the support positions to the clearance of the tester along the object.

SUMMARY OF THE PRESENT INVENTION

The present invention provides a testing device specifically designed to overcome the difficulties encountered with the prior art arrangements and at the same time to provide a thorough testing of the object along which the testing device is moved. More specifically the present invention provides a device for magnetically testing while uninterruptedly moving along an elongated magnetically permeable object having intermittent supports at one side thereof. The device, which is arranged to close around and test the object from all sides other than at the supports and which is adapted to open at and clear past the supports while continuing to move, comprises a housing having first and second housing sections hingedly connected to one another, magnetic field inducing means in the housing, magnetic field sensors in each of the housing sections, means adapted for maintaining the first housing section in a testing position relative to the object with the second housing section being moveable relative to the first housing section for opening and closing the device around the object, actuator means for effecting such opening and closing and control means for operation of the actuator means without manual assistance at the device.

The control means may be in the form of a detector for automatically detecting the supports as they are approached by the device with the actuator means being responsive to the detector to automatically open the housing to allow the device to move past the supports and to thereafter automatically close the housing sections.

Another form of control which can be used in lieu of of in combination with the detector control is a remote manual control for operation of the actuator means without manual assistance directly at the device.

According to an aspect of the present invention the magnetic field inducing means comprises strong permanent magnets spaced apart from one another and confined to the first housing section with the second housing section comprising simply a narrow sensor carrying member located between the magnets substantially free of any magnetic attraction for eliminating magnetic resistance to the opening of the second housing section.

BRIEF DISCUSSION OF THE DRAWINGS

The above as well as other advantages and features of the present invention will be described in greater detail according to the preferred embodiments of the present invention in which.

DETAILED DESCRIPTION ACCORDING TO THE PREFERRED EMBODIMENTS OF THE PRESENT INVENTION

Figure 1:
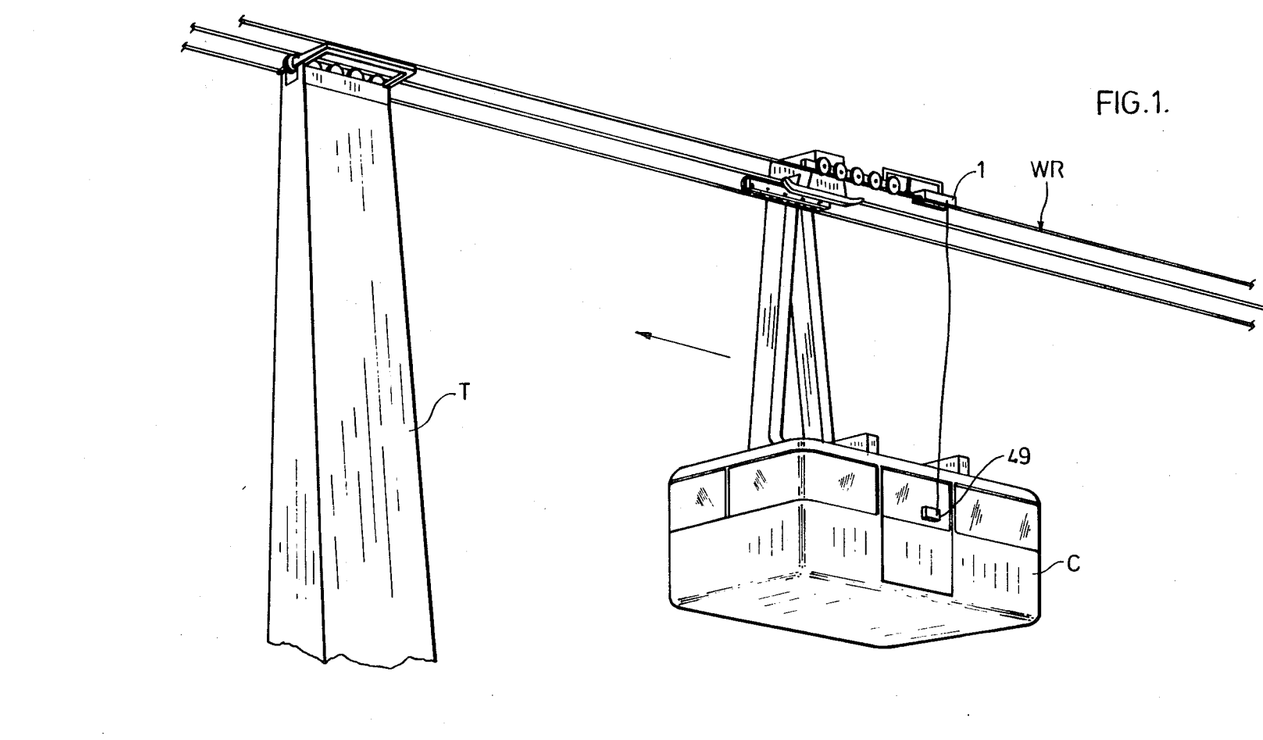
FIG. 1 is a perspective view of a cable car system incorporating a wire rope tester according to a preferred embodiment of the present invention.

FIG. 1 shows a cable car C travelling along and support by a wire rope network WR above the cable car. Secured rearwardly of the cable car and riding along one of the wire ropes is a wire rope testing device 1 which tests for weaknesses along the wire rope. FIG. 1 also shows a supporting tower T for supporting the wire rope network from beneath. The supporting tower therefore blocks the lower half of the wire rope network directly at the tower and the testing device 1 as shown in FIG. 1 is specifically adapted to clear by the tower without anyone having to climb out of the cable car and open the otherwise closed testing device. In fact, testing device 1 is constructed such that the cable car does not have to stop or even slow down at the tower in order to clear the testing device past the tower.

Figure 2:
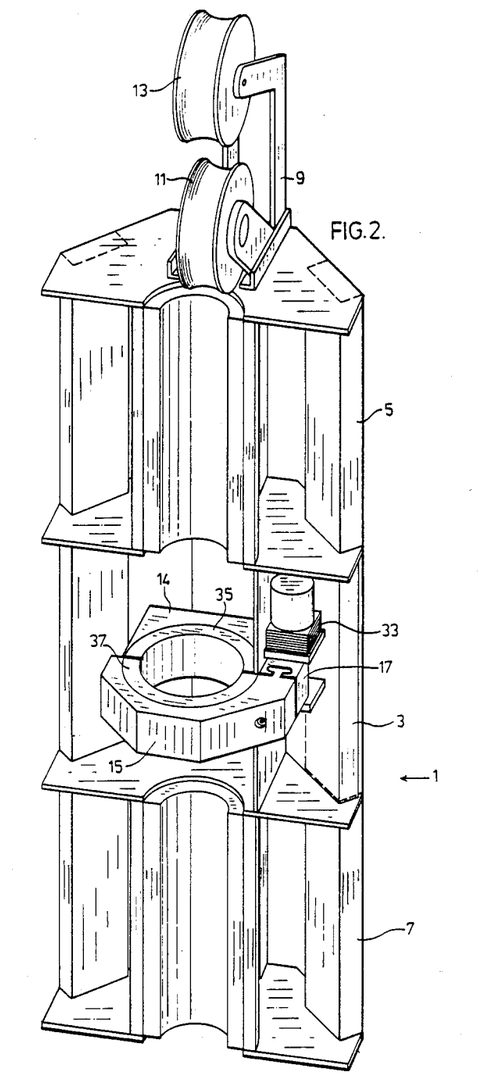
FIG. 2 is a perspective view taken form beneath the wire rope tester of FIG. 1 with the second housing section in the closed position.

Referring to FIG. 2, testing device 1 comprises a major first or upper housing section 3 and a minor second or lower housing section 15, hingedly connected to one another. The upper housing section carries the bulk of the components of the structure and is maintained in a constant testing position relative to the wire rope whereas the lower housing section 15 is arranged only to carry a magnetic field sensing arrangement. Therefore, this lower housing section is extremely light in weight and as such is readily moveable to and from its sensing position.

Figure 3:
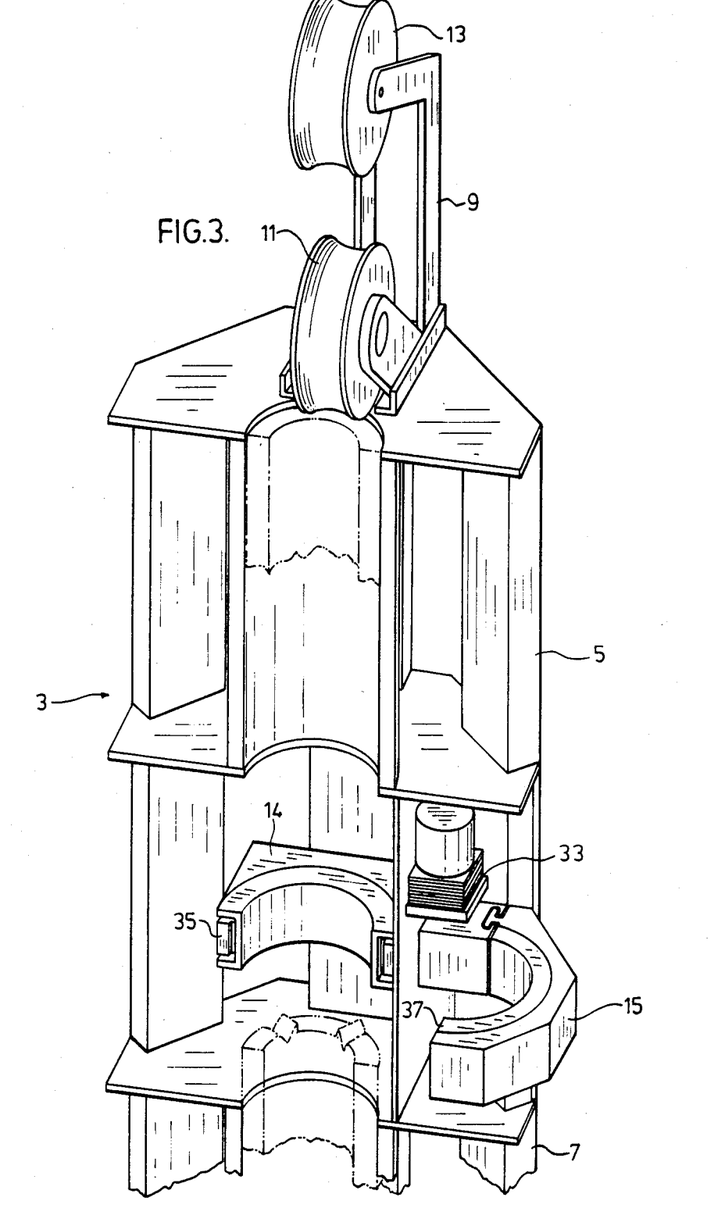
FIG. 3 is a view similar to FIG. 2 with the second housing section in the open position.
Figure 4:
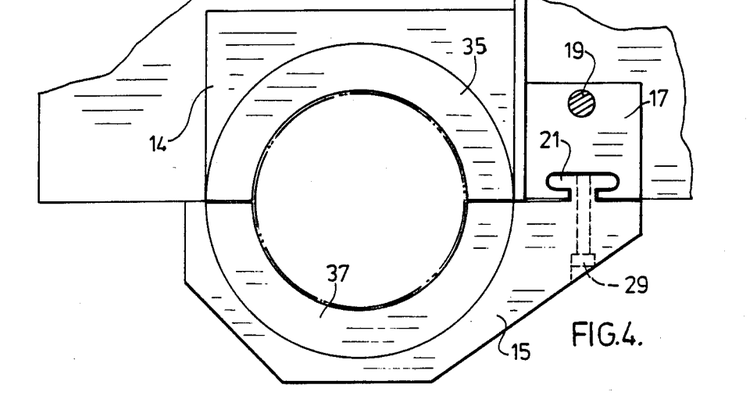
FIGS. 4 and 5 are end views of the second housing section in the closed and open positions respectively.
Figure 5:
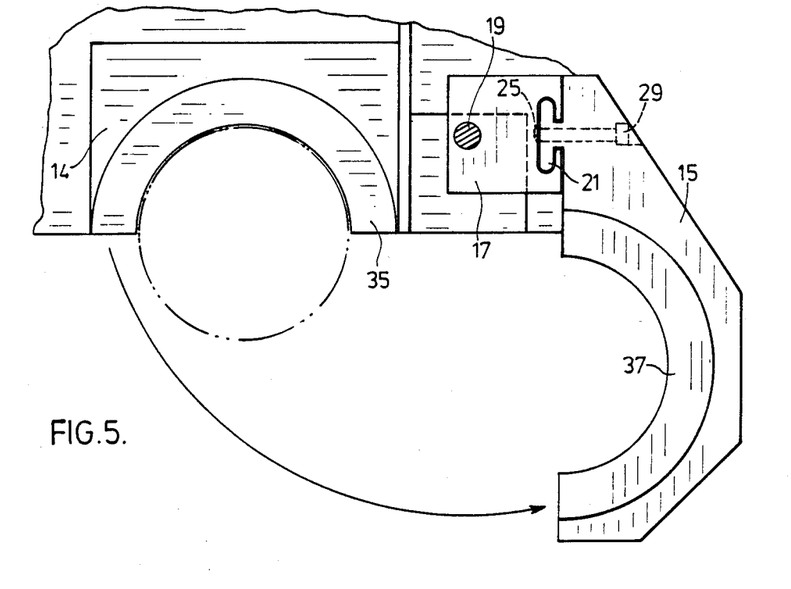

Referring in more detail to FIGS. 2 and 3, the upper housing section comprises forward and rearward pole pieces 5 and 7 which wrap around the upper half of the wire rope. These pole pieces are fitted with strong permanent magnets which act as north and south poles in establishing a magnetic field with the wire rope at the rope section located between the pole pieces. The strength of the magnetic fields emitted from these magnets is quite substantial of magnetically saturating the rope section at the tester without surrounding the rope with magnets as is the case with prior art structures.

The upper housing section is further provided with a forward arm arrangement 9 carrying a guide wheel 11 which sits directly on the wire rope and a distance counter wheel 13 which also sits on the wire rope. As an alternate arrangement these two wheels are replaced by a single combination function wheel. In the event that a weakness is detected along the wire rope, the distance counter wheel is used to indicate the location of the detected weakness through a feedback system to a recording device directly in the cable car which records magnetic fluctuations along the wire rope, detected by testing device 1. The forward arm arrangement is also used to fix the upper housing section to the cable car and to maintain the upper section in a testing position relative to the wire rope.

FIG. 2 shows the lower housing section in its closed position where both the upper and lower housing sections are located in a testing position as would be the case in the expanses of wire rope between the towers. FIG. 3 however, shows the lower housing section in its open position as is required to clear past the towers where the wire rope is blocked from beneath. According to the present invention this movement from the FIG. 2 to the FIG. 3 position and back again is accomplished by an actuator assembly without requiring any manual assistance whatsoever at the housing.

Figure 6:
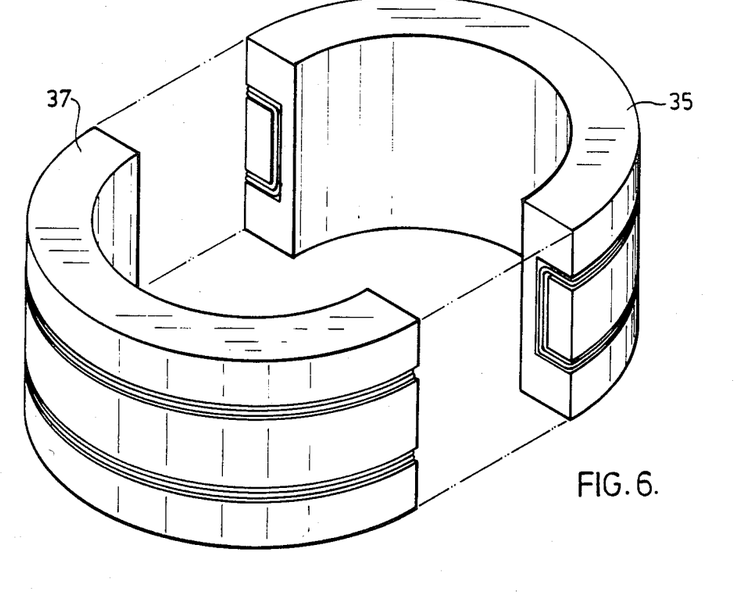
FIG. 6 is an enlarged view of the radial flux leakage search coil used in the structure of FIG. 1 through 5.

Before turning to the opening and closing operation of the lower housing section, reference is had to FIG. 6 showing a pair of loop forming portions 35 and 37 with magnetic coils embedded directly in each of the loop forming portions. Loop portion 35 is located in position in the upper housing section by means of an internal support 14 shown in FIGS. 2 and 3 while loop forming portion 37 is secured along the inner surface of the lower housing section. When the two housing sections are in the closed position, a substantially continuous detector is formed around the rope. This coil moves with the testing device over the rope section which is magnetically saturated in the direction of its axis. Any anomolies in the rope section such as those resulting from broken strands in the rope will cause a radial flux leakage from the main magnetic field which is picked up as it passes through the coil. It is important that the detector substantially completely surround the wire rope since, as a result of the inverse square law, some anomolies on the lower part of the rope away from the upper coil portion may only be detectable by the coil portion in the lower housing section.

It should be noted that the housing can also be fitted with main field sensors which are set up to detect variances in the magnetic field which are indicative of cross-sectional area changes caused for example by deterioration within the rope.

Figures 8, 9:
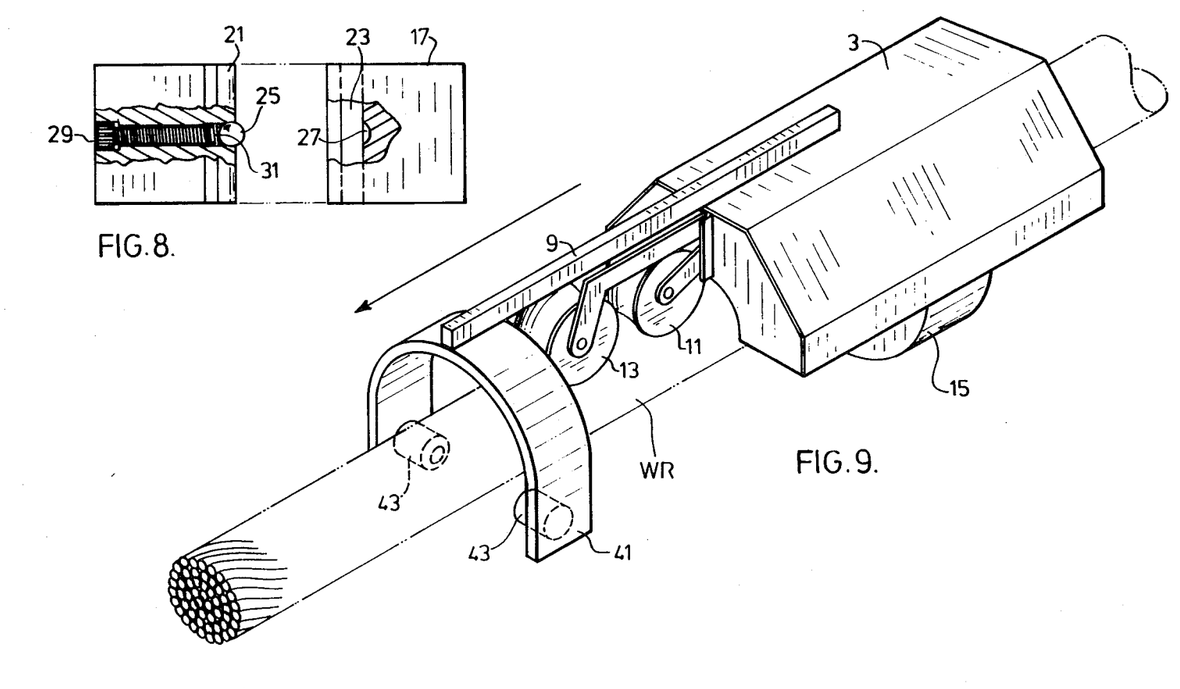
FIG. 8 is a sectional view through the connecting end of the second housing section and the connector shown in FIG. 7 when the two are separated from one another.
FIG. 9 is an enlarged perspective view of the testing device shown in FIG. 1 fitted over the steel wire rope.

The opening and closing of the lower housing section is effected by a motor 33 as shown in the drawings or by a pair of motors mounted on the bottom half of the upper housing section. Each motor may be controlled automatically or by a remote manual control. For automatic motor control, a system as shown in FIG. 9 is provided. This system includes a tower detector 41 forwardly of the testing device and provided with photoelectric sensors 43. These photoelectric sensors are positioned outside of and along the bottom half of the wire rope where they detect the presence of the tower as it passes through the sensors. After the tower has been detected a signal is fed from the detector back to motor 33 for automatically opening the lower housing section to allow the testing device to clear past the tower and to thereafter through the use of an adjustable timer or similar means automatically close the lower housing section beyond the tower. It should be noted that detector 41 is set up such that it also has adequate clearance to ride past the tower.

A second manual remote control 49 as shown in FIG. 1 is also provided for operation of motor 33. This remote control will only be used in the event that there is faulty operation of the detecting device 41. Therefore, if the operator of the system riding in the cable car sees that the lower housing section has not opened as detector 41 senses the tower, he can then remotely control motor 33 through control 49 to automatically open and close the lower housing section without having to climb out of the cable car.

The connection between the first and second housing sections is one which is specifically adapted for use in the testing device of the present invention. This connection which is best shown in FIGS. 4, 5, 7 and 8 is made by means by a connector member 17 mounted to shaft 19 from motor 33. The connector is provided with a an open ended undercut slot 23 for slidably receiving a tongue member 21 forming part of the lower housing section. This tongue and slot arrangement is set up such that in the event that the lower housing section cannot be opened from the cable car and the lower housing section impacts with the tower, tongue 21 will release through the slot 23 in connector 17 to knock the lower housing section from the connector without affecting the upper housing section. This will substantially mitigate any possible damages to the device since, as described above, the bulk of the device components are carried on the upper housing section.

Figure 7:
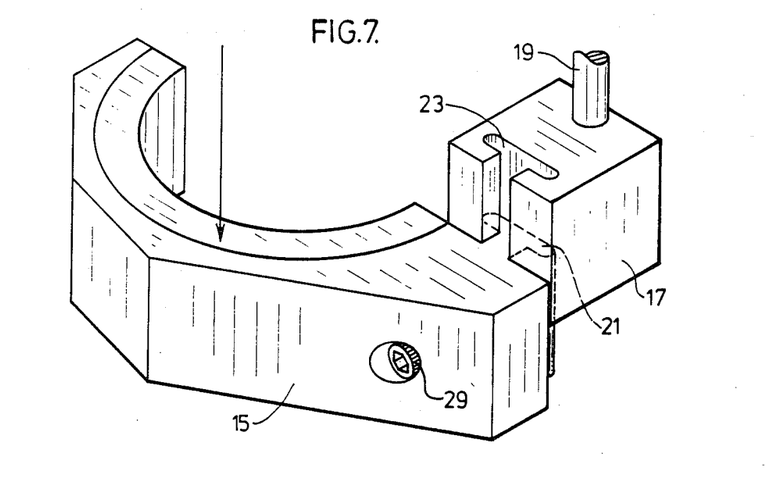
FIG. 7 is an enlarged perspective view of the second housing section and its connection to the first housing section.

An adjustment mechanism is provided for adjusting the frictional contact between tongue 21 and the connector to either reduce or to increase the amount of impact force required to dislodge the lower housing section from the tester. This mechanism comprises a rounded pawl 25 which sits in a semi-circular recess 27 within slot 23 of connector 17. A spring 31 applying outward pressure on pawl 25 and a threaded bolt 29 for adjusting the amount of pressure applied by spring 31 on the pawl are also provided. As the spring pressure is increased so is the amount of force required to slide the lower housing section out of connector 17.

As mentioned above the lower housing section is relatively light in weight which substantially reduces the load placed on motor 33 required to open and close the lower housing section. In addition the lower housing section is located to the center of the testing device between the magnets at either end thereof so that the lower housing section is essentially free of any magnetic resistance to its opening which is totally unlike prior art arrangements in which a substantial separating force is required due to the fitting of attracting magnets in each of the housing sections. Therefore, the amount of work required to open and close the lower housing section has been substantially reduced in accordance with the present invention. In fact according to a preferred embodiment the lower housing section is made from aluminum which further reduces its weight and which eliminates all magnetic pull on the lower housing section since aluminum is a non-magnetic material.

As will be seen from the above, the preferred embodiment wire rope tester for use with a cable car system does not require any manual assistance at the detecting device whatsoever for opening and closing the housing around the wire rope. The cable car is able to move past the supporting towers without having to stop and without necessitating the operator to climb out on the cables while at the same time giving a very effective testing from all sides of the rope other than at the towers where the rope is strengthened from beaneath by the tower itself. It will be appreciated that the testing device is equally useful in other testing arrangements where an elongated magnetic permeable body is supported from one side at intermittent intervals with the testing device being adapted to open up and clear past those intermittent intervals and to thereafter automatically close. Therefore, although various preferred embodiments of the invention have been described herein in detail it will be appreciated by those skilled in the art that variations may be made thereto without departing from the spirit of the invention or the scope of the appended claims.

The embodiments of the invention in which an exclusive property or privilege is claimed are defined as follows:

1. A testing device for magnetically testing while uninterruptedly moving along an elongated magnetically permeable stationary object having intermittent supports at one side thereof, said device being arranged to close around and test the object from all sides other than at the supports and being adapted to open at and clear past the supports while continuing to move, said device comprising a housing having a first major stationary housing section and a minor moveable housing section hingedly connected thereto, magnetic field sensors in each of said housing sections, means for maintaining said first housing section in a testing position while said second housing section is moved relative to the object for opening and closing said device therearound, actuator means for effecting such opening and closing, control means for operation of said actuator means without manual assistance at the device, and magnetic field inducing means comprising strong permanent magnets spaced apart from one another and pole pieces for directing the magnetic field from said magnets into the object at said device, said magnetic field inducing means and pole pieces being confined to said first housing section; said second housing section being of a size to fit inwardly between said magnets on said first housing section free of magnetic attraction thereto for eliminating magnetic resistance to opening of said second housing section and being of a reduced weight relative to said first housing section for readily enabling closure of said second housing section by said actuator means.

2. A device as claimed in claim 1 wherein said control means includes detector means for detecting the support as they are approached by said device, said actuator means being responsive to said detector means to automatically open said housing to allow said device to move past the supports and to thereafter automatically close said housing sections.

3. A device as claimed in claim 1 wherein said control means includes a remote manual control for operation of said actuator means.

4. A device as claimed in claim 1 including connecting means for connecting said first and second housing sections, said connecting means being adapted to release said second housing section in the event of impact with the supports for mitigating damage to the device.

5. A testing device for magnetically testing while uninterruptedly moving along a steel wire rope of an aerial cable car system having intermittent support towers beneath the steel wire rope, said testing device being arranged to close around the rope other than at the support towers while continuing to move, said deivce comprising a housing having major upper and minor lower housing sections hingedly connected to one another, magnetic field inducing means and pole pieces confined in said upper housing section, magnetic field sensors in each of said housing sections, means adapted for maintaining said upper housing section in a testing position relative to the rope with said lower housing section being moveable relative to said upper housing section for opening and closing said device around the object, actuator means for effecting such opening and closing and control means for operation of said actuator means without manual assistance at the device, said lower housing section comprising a radial field sensor carrying arm free of magnetic attraction and of a reduced size and weight relative to said upper housing section for eliminating magnetic resistance to opening and easing closure of said lower housing section and a releasable connection between said upper and lower housing section for releasing said lower housing section from said testing device in the event of impact with the support towers.

6. A testing device as claimed in claim 5 wherein said releaseable connection comprises an open ended groove and tongue arrangement where the tongue is slideable into and out of the open ended groove.

7. A testing device as claimed in claim 6 including a spring loaded mechanism for maintaining said tongue in said groove.

8. A testing device as claimed in claim 7 including means for adjusting pressure of said spring loaded mechanism.

9. A testing device as claimed in claim 5 including detector means for automatically detecting the support towers, said actuator means being responsive to said detector means to open said lower housing section for clearing past the towers and to thereafter close the lower housing section.

10. A testing device as claimed in claim 5 including a remote manual control for operation of said actuator means for opening and closing said lower housing section.

11. A testing device as claimed in claim 5, including a hinge connector between said upper and lower housing sections, said actuator means comprising a motor for hinging said connector to effect opening and closing of said lower housing section.

* * * * *